United States Patent [19]

Norcini et al.

[11] Patent Number: 5,438,046
[45] Date of Patent: Aug. 1, 1995

[54] N-HETEROARYL SUBSTITUTED DERIVATIVES OF PROPANAMIDE USEFUL IN THE TREATMENT OF CARDIOVASCULAR DISEASES

[75] Inventors: Gabriele Norcini, Vizzola Ticino; Francesco Santangelo, Milan, both of Italy

[73] Assignee: Zambon Group S.p.A., Vicenza, Italy

[21] Appl. No.: 280,675

[22] Filed: Jul. 27, 1994

[30] Foreign Application Priority Data

Jul. 30, 1993 [IT]   Italy ................. MI93A1772

[51] Int. Cl.$^6$ ............ A61K 31/675; C07F 9/06; C07F 9/02
[52] U.S. Cl. ..................... 514/89; 514/91; 514/92; 546/22; 548/116; 548/119; 548/413
[58] Field of Search ............ 546/22; 548/119, 413, 548/116; 514/89, 91, 92

[56] References Cited

U.S. PATENT DOCUMENTS 4,513,009   4/1985   Roques et al. ............. 514/513
4,618,708  10/1986   Roques et al. ............. 562/448
4,749,688   6/1988   Haslanger et al. .......... 514/19

FOREIGN PATENT DOCUMENTS 0419327   3/1991   European Pat. Off. .
0511940  11/1992   European Pat. Off. .
0117429   9/1994   European Pat. Off. .
1576161  10/1980   United Kingdom .
  13944   8/1992   WIPO .
9311154   6/1993   WIPO .

OTHER PUBLICATIONS

Clavell et al., Supplement V. Circulation, vol. 87, No. 5, 1993, p. 45.
Schwartz et al., Life Science, vol. 1, 47, pp. 1279–1297 (1990).
Umezawa, Sumio, et al., Tetrahydron Letters, No. 1, pp. 97–100 (1972)—"A New Microbial Metabolite Phosphoramidon (Isolation and Structure)".
Matsumura, Yasuo, et al., European Journal of Pharmacology, 185, (1990), pp. 103–106—"Phosphoramidon, A Metalloproteinase Inhibitor, Suppresses the Hypertensive . . . ".
Roques, B. P., et al., Nature, vol. 288, (Nov. 1980), pp. 286–288, "The Enkephalinase Inhibitor Thiorphan Shows Antinociceptive Activity in Mice".
Sy, Michel, et al., Bull. Soc. Chim. Fr., (1963), pp. 1276–1277, "Synthese D'Un Acide Thiophenique Amine".
Lee, Moses, et al., J. Org. Chem. (1988), 53, No. 9, pp. 1855–1859, "Total Synthesis and Absolute Configuration of the Antiobiotic Oligopeptides (4S)-(+)-Anthelvencin A and Its . . . ".
Auguet, Michel, et al., European Journal of Pharmacology, 224 (1992), pp. 101–102, "The Vasoconstrictor Action of Big Endothelin-1- is Phosphoramidon-Sensitive in . . . ".
Llorens, Catherine, et al., European Journal of Pharmacology, 69 (1981), pp. 113–116, "Enkephalinase Activity in Rat Peripheral Organs".

*Primary Examiner*—Cecilia Tsang
*Attorney, Agent, or Firm*—Stevens, Davis, Miller & Mosher

[57] ABSTRACT

Compounds of formula

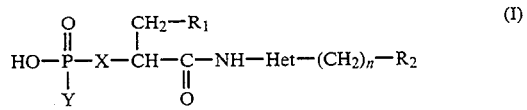

wherein Y, $R_1$, $R_2$, Het, X and n have the meanings reported in the description, processes for their preparation and pharmaceutical compositions which contain them as active ingredients are described. The compounds of formula I are useful in the treatment of cardiovascular diseases.

7 Claims, No Drawings

N-HETEROARYL SUBSTITUTED DERIVATIVES OF PROPANAMIDE USEFUL IN THE TREATMENT OF CARDIOVASCULAR DISEASES

The present invention relates to N-heteroaryl substituted derivatives of propanamide useful in the treatment of cardiovascular diseases and, more particularly, it relates to N-heteroaryl substituted phosphorylated derivatives of propanamide useful in the treatment of cardiovascular diseases as inhibitors of the metabolism of vasoactive peptides.

The pharmacologic interest towards the study of molecules which inhibit the metabolism of vasoactive peptides derives from the role that said peptides exert on the cardiocirculatory system.

For instance, among the inhibitors of the metabolism of vasoactive peptides, the so-called ECE-inhibitors and NEP-inhibitors hold particular interest.

In particular, ECE-inhibitors are able to inhibit the endothelin converting enzyme (ECE), which is responsible for the transformation of big-endothelin into endothelin, a 21 amino acid peptide with vasoconstrictor activity.

NEP-inhibitors, instead, are able to inhibit the neutral endopeptidase enzyme (NEP), also called enkephalinase, which is responsible for the inactivation not only of endogenous enkephaline, but also of the atrial natriuretic factor (ANF), a vasodilator hormone secreted by heart.

Therefore, both ECE-inhibitors and NEP-inhibitors are useful in therapy in the treatment of hypertension, renal failure and congressive heart failure.

The molecule which is considered the parent of the ECE-inhibitors is phosphoramidon [N-[N-[[(6-deoxy-α-L-mannopyranosyl)oxy]hydroxyphos-phinyl]-l-leucyl]-L-tryptophan], first isolated as microbial metabolite [Umezawa et al., Tetrahedron Letters, No. 1, pages 97–100, (1972)] and subsequently studied as inhibitor of the metabolism of vasoactive peptides [see, for instance, Matsumura et al., European Journal of Pharmacology, 185 (1990), 103–106].

The molecule which is considered the parent of the NEP-inhibitors is thiorphan [DL-(3-mercapto-2-benzyl-propanoyl)glycine] first described by Roques et al. in Nature, Vol. 288, pages 286–288, (1980).

The European patent application N. 0419327 (Societé Civile Bioprojeer) describes, among others, some phosphorylated derivatives of amino acids endowed with both inhibitory activity on enkephalinase and ACE (angiotensin converting enzyme).

We have now found N-heteroaryl substituted phosphorylated derivatives of propanamide endowed with both ECE-inhibitory and NEP-inhibitory a activity.

Therefore object of the present invention are the compounds of formula

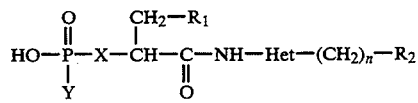

(I)

wherein
Y is a $C_1$–$C_4$ alkyl group or an OR group; R is a hydrogen atom, a $C_1$–$C_4$ alkyl group or a phenylalkyl group having from 1 to 4 carbon atoms in the alkyl moiety;

$R_1$ is a hydrogen atom, a phenyl group, a biphenyl group or a 5 or 6 membered heterocycle containing 1 or 2 heteroatoms selected among nitrogen, oxygen and sulphur, optionally substituted by one or two groups selected among $C_1$–$C_4$ alkyl or alkoxy groups, hydroxy, halogen or trifluoromethyl groups;

$R_2$ is a carboxylic group or a $COOR_3$ or

group; $R_3$ is a $C_1$–$C_4$ alkyl group or a phenylalkyl having from 1 to 4 carbon atoms in the alkyl moiety; $R_4$ and $R_5$, the same or different, are hydrogen atoms, $C_1$–$C_4$ alkyl or $C_5$–$C_7$ cycloalkyl groups;

n is 0 or 1;

Het is a heterocycle selected among thiazole, oxazole, isothiazole, isoxazole, pyrazole, imidazole, thiophene, pyrrole and pyridine.

X is NH or $CH_2$;

and their pharmaceutically acceptable salts.

The compounds of formula I have at least one asymmetric carbon atom and may therefore exist in the form of stereoisomers.

The compounds of formula I, ether in the form of stereoisomeric mixture or in the form of single stereoisomers, are object of the present invention.

The compounds of formula I are endowed with both ECE-inhibitory and NEP-inhibitory activity and are useful in the treatment of cardiovascular diseases such as hypertension, renal failure and congestive heart failure.

In the present description, unless otherwise specified, with the term $C_1$–$C_4$ alkyl we intend a straight or branched $C_1$–$C_4$ alkyl such as methyl, ethyl, n.propyl, isopropyl, n.butyl, isobutyl, sec.butyl and t.butyl; with the term $C_5$–$C_7$ cycloalkyl we intend cyclopentryl, cyclohexyl and cycloheptyl; with the term biphenyl we intend a 2-biphenyl, 3-biphenyl and 4-biphenyl group; with the term $C_1$–$C_4$ alkoxy we intend a straight or branched $C_1$–$C_4$ alkoxy such as methoxy, ethoxy, n/propoxy, isopropoxy, n.butoxy, isobutoxy, sec.butoxy and t.butoxy.

With the term 5 or 6 membered heterocycle containing 1 or 2 heteroatoms selected among nitrogen, oxygen and sulphur we intend a heteroatoms selected among nitrogen, oxygen and sulphur we intend a heterocycle preferably selected among thiazole, oxazole, isothiazole, isoxazole, pyrazole, imidazole, thiophene, pyrrole and pyridine.

Examples of pharmaceutically acceptable salts of compounds of formula I are the salts with alkali metals or alkali-earth metals. A class of preferred compounds comprises the compounds of formula I wherein Y is an OR group, R is a hydrogen atom, a methyl or benzyl group and R2 is a carboxylic group.

Still more preferred compounds are the compounds of formula I wherein Y is an OR group, R is a hydrogen atom, a methyl or benzyl group; $R_2$ is a carboxylic group; $R_1$ is phenyl and Her is a heterocycle selected between thiazole and pyridine.

Another class of preferred compounds comprises the compounds of formula I wherein Y is a $C_1$–$C_4$ alkyl group; $R_2$ is a carboxylic group; $R_1$ is a phenyl group, optionally substituted by one or two halogen atoms, a biphenyl group or a heterocycle selected between thiazole and thiophene and Her is a heterocycle selected between thiazole, pyrrole and pyridine.

Still more preferred compounds in this class are the compounds of formula I wherein Y is n.propyl; $R_2$ is a carboxylic group; $R_1$ is a phenyl group, optionally substituted by one or two halogen atoms, a 4-biphenyl group or a heterocycle selected between thiazole and thiophene and Her is a heterocycle selected between thiazole, pyrrole and pyridine.

Preferred examples of pharmaceutically acceptable salts of compounds of formula I are the salts with alkali metals such as sodium, lithium and potassium.

The compounds of formula I wherein $R_2$ is a $COOR_3$ or

group can be converted into the organism to the corresponding compounds of formula I wherein $R_2$ is a carboxylic group ($R_2$=COOH).

In this case, the ester or the amide derivative wherein $R_2$ is a $COOR_3$ or

group respectively are prodrugs of the corresponding compounds wherein $R_2$ is a carboxylic group.

The preparation of the compounds of formula I wherein X is NH, which ape the object of the present invention, comprises the condensation between an amino acid of formula

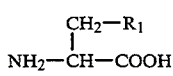 (II)

wherein $R_1$ has the above reported meanings; and a compound of formula

H₂H-Het-(CH₂)ₙ-R₂ (III)

wherein $R_2$, Her and n have the above reported meanings.

The condensation is carried out according to conventional techniques of the chemistry of peptides and comprises the optional protection of the amino group of the compound of formula II and of the carboxylic group of the compound of formula III ($R_2$=COOH).

After removal of the optional protecting group of the compound of formula II according to usual methods the obtained intermediate of formula

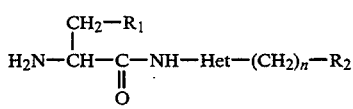 (IV)

wherein $R_1$, $R_2$, Her and n have the above reported meanings; is phosphorylated by reaction with a phosphorylating agent of formula

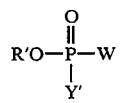 (V)

wherein

Y' is a $C_1$-$C_4$ alkyl group or an OR' group, R' is a $C_1$-$C_4$ alkyl group, a phenyl group or a phenylalkyl group having from 1 to 4 carbon atoms in the alkyl moiety and W is a halogen atom, preferably chlorine.

After total or partial removal of the protecting groups the compounds of formula I wherein X is NH are obtained.

The compounds of formula I wherein X is $CH_2$ are prepared starting from the compounds of formula

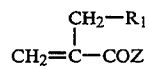 (VI)

wherein Z is a halogen atom, preferably chlorine or bromine and $R_1$ has the above reported meanings; by reaction with an intermediate of formula III in a suitable solvent and in the presence of a base.

Preferably the compounds of formula III are used in a protected form ($R_2$=$COOR_3$ or

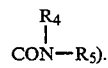).

The thus obtained intermediate t,0073 wherein $R_1$, $R_2$, Her and n have the above reported meanings; is then phosphorylated by reaction with a phosphorylating agent of formula

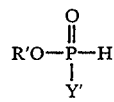 (VIII)

wherein Y' and R' have the above reported meanings.

After total or partial removal of the protecting groups the compounds of formula I wherein X is $CH_2$ are obtained.

The intermediates of formula III are known or easily prepared with known methods.

For a bibliographic reference to the preparation of the compounds of formula III see for instance Michel Sy et al., Bull. Soc. Chim. Ft., 1276–1277, (1963) and Moses Lee et al., J. Org. Chem., 53, N. 9, 1855–1859, (1988).

The compounds of formula VI are known or easily prepared according to conventional methods (see for instance the British patent n. 1576161 in the name of Squibb E. R. & Sons Inc.) from the corresponding acids of formula

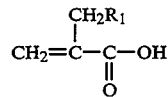 (IX)

wherein $R_1$ has the above reported meanings.

The compounds of formula I in the form of single stereoisomers are prepared by stereoselective synthesis or by separation of the stereoisomeric mixture according to conventional techniques.

The compounds of formula I are active as ECE-inhibitors and NEP inhibitors and are useful in the treatment of cardiovascular diseases such as hypertension, renal failure and congestive heart failure.

The ECE-inhibitory activity of the compounds of formula I was evaluated by means of in vitro tests for the inhibition of endothelin formation and resulted to be significantly greater than that of phosphoramidon (see example 52).

The NEP-inhibitory activity of the compounds of formula I was evaluated by means of in vitro tests as percentage of inhibition in the formation of [$^3$H]-Tyr-Gly-Gly, a metabolite of [$^3$H][Leu$^5$]-enkephaline and resulted to be substantially comparable with that of thiorphan (see example 52).

For a practical use in therapy the compounds of formula I can be formulated in solid or liquid pharmaceutical compositions, suitable for oral or parenteral administration.

Therefore, the pharmaceutical compositions containing one or more compounds of formula I, as active ingredient, in admixture with a carrier for pharmaceutical use are a further object of the present invention.

Specific examples of the pharmaceutical compositions according to the present invention are tablets, coated tablets, capsules, granulates, solutions and suspensions suitable for oral administration, solutions and suspensions suitable for parenteral administration.

In the pharmaceutical compositions object of the present invention one or more compounds of formula I may be associated with other active ingredients such as for instance ACE-inhibitors. The pharmaceutical compositions object of the present invention are prepared according to conventional techniques.

The daily dose of compound of formula I depends on different factors such as the seriousness of the disease, the individual response of the patient, the use of biological precursors and the kind of formulation but it is usually comprised between 0.1 mg and 100 mg per Kg of body weight divided into a single dose or into more daily doses. With the aim of better illustrating the present invention the following examples are now given.

EXAMPLE 1

Preparation of
N-(4-ethoxycarbonylmethyl-2-thiazolyl)-2-benzyloxycarbonylamino-3-phenyl-propanamide A solution of N-benzyloxycarbonyl-L-phenylalanine (19.5 g; 0.0652 moles), carbonyldiimidazole (10.7 g; 0.0660 moles) in anhydrous tetrahydrofuran (250 ml) was kept under stirring at 22° C. for 30 minutes under nitrogen.

Ethyl (2-amino-4-thiazolyl)acetate (12.13 g; 0.0652 moles) was then added portionwise.

After 18 hours at 22° C., the solvent was evaporated under vacuum and an oil was obtained.

After purification by chromatography on silica gel (eluent hexane:ethyl acetate=:1), N-(4-ethoxycarbonylmethyl-2-thiazolyl)-2-benzyloxycarbonylamino-3-phenyl-propanamide (18 g; 60% yield) was obtained as oil which solidifies.

$^1$H-NMR (300 MHz, CDCl$_3$): δ (ppm): 1.20 (t, 3H); 3.10 (m, 2H); 3.60 (s, 2H); 4.10 (q, 2H); 4.86 (m, 1H); 5.05 (dd, 2H); 5.84 (bd, 1H); 6.80 (s, 1H); 7.00–7.40 (m, 10H).

Alternatively, by working in a way similar to that above reported and by using N-tert-butoxycarbonyl-L-phenylalanine (10 g; 37.7 mmoles), N-hydroxysuccinimide (4.78 g; 41.5 mmoles), dicyclohexylcarbodiimide (8.56 g; 41.5 mmoles) and ethyl (2-amino-4-thiazolyl)acetate (7 g; 37.7 mmoles), a crude was obtained which, chromatographed on silica gel (eluent ligroin:ethyl acetate 6:4) and further crystallized from ligroin, afforded N-(4-ethoxycarbonylmethyl-2-thiazolyl)-3-phenyl-2-(tert-butoxycarbonyl)amino-propanamide (13.74 g; 84.14% yield).

m.p. 119°–120° C.

$^1$H-NMR (300 MHz, CDCl$_3$): δ (ppm): 1.22 (t, 3H); 1.35 (s, 9H); 3.06 (dd, 1H); 3.24 (dd, 1H); 3.65 (s, 2H); 4.14 (q, 2H); 4.63 (bs, 1H); 5.01 (bs, 1H); 6.80 (s, 1H); 7.12–7.29 (m, 5H); 9.79 (s, 1H).

EXAMPLE 2

Preparation of
N-(4-ethoxycarbonylmethyl-2-thiazolyl)-2-amino-3-phenyl-propanamide Iodotrimethylsilane (20.4 ml) was added at 0° C. and under nitrogen to a solution of N-(4-ethoxycarbonylmethyl-2-thiazolyl)-2-benzyloxycarbonylamino-3-phenyl-propanamide (16.75 g; 0.0358 moles), prepared as described in example 1, in acetonitrile (335 ml).

After one hour at room temperature, the reaction mixture was evaporated under vacuum.

The residue was collected with HCl 1N and water and washed twice with ethyl ether.

After reaching the pH of about 8–9 with a solution of KOH at 10%, the aqueous phase was extracted with ethyl acetate.

The organic phase was dried on sodium sulphate and the solvent was evaporated thus obtaining a crude which was purified by chromatography on silica gel column (eluent CH$_2$Cl$_2$:CH$_3$OH=95:5) and then crystallized as hydrochloride from ethanol.

N-(4-ethoxycarbonylmethyl-2-thiazolyl)-2-amino-3-phenyl-propanamide hydrochloride (3.3 g; 26% yield) was obtained as white solid.

$^1$H-NMR (200 MHz, DMSO-d$_6$): δ (ppm): 1.20 (t, 3H); 3.18 (m, 2H); 3.69 (s, 2H); 4.08 (q, 2H); 4.27 (m, 1H); 7.08 (s, 1H); 7.28 (m, 5H).

Alternatively, by deprotecting N-(4-ethoxycarbonylmethyl-2-thi-azolyl)-3-phenyl-2-(tert-butoxycarbonyl)amino-propanamide (5 g; 11.5 mmoles), prepared as described in example 1, in the presence of trifluoroacetic acid, N-(4-ethoxycarbonylmethyl-2-thiazolyl)-2-amino-3-phenyl-propanamide (3.6 g; 93.2% yield) having the same above reported spectroscopic characteristics, was obtained.

EXAMPLE 3

Preparation of
N-(4-ethoxycarbonylmethyl-2-thiazoly)-2-dibenzyloxyphosphinylamino-3-phenyl-propanamide.

A solution of dibenzyl chlorophosphonate (2.3 g; 0.0078 moles) in toluene (20 ml) was added dropwise to a solution of N-(4-ethoxycarbonylmethyl-2-thiazolyl)-2-amino-3-phenyl-propanamide (2.6 g; 0.078 moles), prepared as described in example 2, and triethylamine (1 ml; 0.0078 moles) in anhydrous toluene (100 ml), kept under stirring and under nitrogen at 22° C.

After 2 hours, the reaction mixture was poured into water (100 ml) and the organic phase separated.

The aqueous phase was extracted with ethyl acetate and the collected organic phases were dried on sodium sulphate.

After evaporating the solvent under vacuum a crude was obtained which, crystallized from ethyl acetate:-hexane=1:1, afforded N-(4-ethoxycarbonylmethyl-2-thiazolyl)-2-dibenzyloxyphoxyphosphinylamino-3-phenyl-propanamide (2.5 g; 53.3% yield).

$^1$H-NMR (200 MHz, CDCl$_3$): δ (ppm): 1.13 (t, 3H); 3.03 (d, 2H); 3.61 (s, 2H); 4.12 (q, 2H); 4.20 (m, 1H); 4.68 (m, 2H); 4.88 (m, 2H); 6.80 (s, 1H); 7.02–7.31 (m, 15H).

EXAMPLE 4

Preparation of N-(4-Carboxymethyl1-2-thiazoly)-2-dibenzyloxyphosphinylamino-3-phenyl-propanamide A solution of N-(4-ethoxycarbonylmethyl-2-thiazolyl)-2-dibenzyloxyphosphinylamino-3-phenyl-propanamide (1.65 g; 0.0028 moles), prepared as described in example 3, and sodium hydroxide 98% (0.445 g; 0.0111 moles) in a mixture water:methanol=1:1 (8 ml) was kept under reflux for two hours.

After cooling, the reaction mixture was treated with HCl 1N till pH of about 1.

After extraction with ethyl acetate and washing with water, the organic phase was dried on sodium sulphate.

The solvent was evaporated to dryness affording N-(4-carboxymethyl-2-thiazolyl)-2-dibenzyloxyphosphinylamino-3-phenyl-propanamide (1.8 g) as rough material which was used in the subsequent reaction without further purifications.

EXAMPLE 5

Preparation of N-(4-carboxymethyl-2-thiazolyl)-2-benzyloxyhydroxyphosphinylamino-3-phenyl-propanamide (Compound 1)

A solution of N-(4-carboxymethyl-2-thiazolyl)-2-dibenzyloxyphosphinylamino-3-phenyl-propanamide (1.4 g; 0.0025 moles), prepared as described in example 4, and sodium iodide (1.48 g; 0.0099 moles) in acetone (30 ml) was heated under reflux for 4 hours.

After cooling, the precipitate was eliminated and the solvent evaporated to dryness.

The residue was collected with ethyl acetate and water.

The organic phase was separated and concentrated obtaining a precipitate which was filtered and dried under vacuum.

N-(4-carboxymethyl-2-thiazolyl)-2-benzyloxyhydroxyphosphinylamino-3-phenyl-propanamide (0.15 g; 12.7% yield) was obtained as white solid.

m.p. 195°–197° C.

$^1$H-NMR (300 MHz, D$_2$O): δ (ppm): 3.25 (m, 2H); 3.81 (bs, 2H); 4.54 (bt, 1H); 7.14–7.35 (m, 6H).

EXAMPLE 6

Preparation of N-(4-ethoxycarbonylmethyl-2-thiazolyl)-2-benzolyl)-2-propenamide

2-Benzyl-2-propenoic acid (13 g; 0.080 moles) was dissolved in thionyl chloride (13 ml).

After 24 hours at 20° C., the reaction mixture was evaporated to dryness and the residue was collected twice with toluene (50 ml), evaporating to dryness each time.

An oil was obtained which was collected with pyridine (20 ml) and a solution of ethyl (2-amino-4-thiazolyl)acetate (14.92 g; 0.080 moles) in pyridine (160 ml) was added dropwise under nitrogen atmosphere.

After one hour at room temperature the solvent was evaporated under vacuum and by chromatography on silica gel column (eluent hexane:ethyl acetate=6.4) N-(4-ethoxycarbonylmethyl-2-thiazolyl)-2-benzyl-2-propenamide (20 g; 75.6% yield) was obtained as oil.

$^1$H-NMR (200 MHz, CDCl$_3$): δ (ppm): 1.24 (t, 3H); 3.65 (s, 2H); 3.74 (s, 2H); 4.16 (q, 2H); 5.46 (m, 1H); 5.94 (s, 1H); 6.78 (s, 1H); 7.25 (m, 5H).

EXAMPLE 7

Preparation of N-(4-methoxycarbonylmethyl-2-thiazolyl)-2-benzyl-2-propenamide

A solution of sodium methylate obtained from metallic sodium (4 g; 0.175 moles) in methanol (100 ml) was added to a solution of N-(4-ethoxycarbonylmethyl-2-thiazolyl)-2-benzyl-2-propenamide (19.35 g; 0.0610 moles), prepared as described in example 6, and dimethyl phosphite (6.44 g; 0.0585 moles) in anhydrous methanol (250 ml). After one hour at room temperature, the reaction mixture was diluted with water and the pH was brought to 7.5–8.

Methanol was evaporated and the aqueous phase was extracted with ethyl acetate.

The organic phase was dried on sodium sulphate and the solvent was evaporated to dryness.

The obtained oil was purified by chromatography on silica gel (eluent hexane:ethyl acetate=6:4) affording N-(4-methoxycarbonylmethyl-2-thiazolyl)-2-benzyl-2-propenamide (15.5 g; 83.8% yield) as oil.

$^1$H-NMR (200 MHz, CDCl$_3$): δ (ppm) 3.65 (s, 2H); 3.67 (s, 3H); 3.74 (s, 2H); 5.44 (m, 1H); 5.91 (s, 1H); 6.77 (s, 1H); 7.25 (m, 5H).

EXAMPLE 8

Preparation of N-(4-methoxycarbonylmethyl-2-thiazolyl)-2-benzyl-3-dimethoxyphsophinyl-propanamide A solution of dimethyl phosphite (5.4 g; 0.049 moles) and then a solution of N-(4-methoxycarbonylmethyl-2-thiazolyl)-2-benzyl-2-propenamide (15.5 g; 0.049 moles), prepared as described in example 7, in anhydrous tetrahydrofuran (150 ml) were added dropwise to a suspension of sodium hydride at 60% in oil (2.16 g; 0.054 moles) in anhydrous tetrahydrofuran, kept under stirring at 0° C. under nitrogen.

The reaction mixture was left at room temperature for 48 hours, then the solvent was evaporated under vacuum.

The residue was collected with water and extracted with ethyl acetate (2×200 ml).

The organic phase was dried on sodium sulphate ad the solvent was evaporated to dryness.

The obtained crude was purified by chromatography on silica gel (eluent CH$_2$Cl$_2$:CH$_3$OH=95:5) affording N-(4-methoxycarbonylmethyl-2-thiazolyl)-2-benzyl-3-dimethoxyphosphinyl-propanamide (9.5 g; 45.5% yield) as oil.

$^1$H-NMR (200 MHz, CDCl$_3$): δ (ppm): 1.94 (m, 1H); 2.32 (m, 1H); 2.73 (m, 1H); 3.06 (m, 1H); 3.28 (m, 1H); 3.52–3.67 (m, 11H); 6.72 (s, 1H); 7.13 (m, 5H).

EXAMPLE 9

Preparation of
N-(4-carboxymethyl-2-thiazolyl)-2-benzyl-3-hydroxymethoxyphosphinyl-propanamide (Compound 2)

A solution of N-(4-methoxycarbonylmethyl-2-thiazolyl)-2-benzyl-3-dimethoxyphosphinyl-propanamide (3.45 g; 8.09 mmoles) in HCl 37% (70 ml) was heated at 60° C. for 6 hours.

After cooling and evaporating the solvent under vacuum the residue was collected with acetone and the solution was decolorized with activated carbon.

The solvent was evaporated to dryness and the residue was collected with water affording N-(4-carboxymethyl-2-thiazolyl)-2-benzyl-3-hydroxymethoxyphosphinyl-propanamide (1.3 g; 40.33% yield) as white solid.

$^1$H-NMR (200 MHz, DCl): δ (ppm): 2.10–2.60 (m, 2H); 2.95–3.25 (m, 2H); 3.30–3.50 (m, 1H); 3.67 (d, 3H); 4.00 (s, 2H); 7.20–7.45 (m, 6H).

EXAMPLE 10

Preparation of
N-(4-methoxycarbonyl-2-pyridyl)-2-benzyl2-propenamide

By working in a way similar to that described in example 6 and by starting from methyl 2-amino-isonicotinate (9.35 g), after chromatography on silica gel (eluent hexane:ethyl acetate=7:3), N-(4-methoxycarbonyl-2-pyridyl)-2-benzyl-2-propenamide (10 g; 55% yield) was obtained as oil.

$^1$H-NMR (300 MHz, CDCl$_3$): δ (ppm): 3.78 (s, 2H); 3.95 (s, 3H); 5.48 (bs, 1H); 5.95 (s, 1H); 7.20–7.40 (m, 5H); 7.60 (dd, 1H); 8.31 (bs, 1H); 8.38 (d, 1H); 8.88 (s, 1H).

EXAMPLE 11

Preparation of
N-(4-methoxycarboyl-2-pyridyl)-2-benzyl-3-dimethoxyphosphinyl-propanamide A solution of sodium methylate obtained by dissolving metallic sodium (0.156 g) in anhydrous methanol (30 ml) was added dropwise under nitrogen atmosphere to a solution of N-(4-methoxycarbonyl-2-pyridyl)-2-benzyl-2-propeamide (1 g; 0.0034 moles), prepared as described in example 10, and dibenzyl phosphite (0.885 g; 0.0034 moles) in anhydrous methanol (25 ml).

After one night at room temperature, the reaction mixture was poured into ammonium chloride at 5% (100 ml).

Methanol was evaporated under vacuum and the aqueous phase was extracted with ethyl acetate.

The organic phase was dried on sodium sulphate and the solvent evaporated under vacuum.

The oily residue was chromatographed on silica gel (eluent CH$_2$Cl$_2$: CH$_3$OH=95:5) affording N-(4-methoxycarbonyl-2-pyridyl)-2-benzyl-3-dimethoxyphosphinyl-propanamide (1 g; 72.8% yield) as oil.

$^1$H-NMR (200 MHz, CDCl$_3$): δ (ppm): 1.80–2.05 (m, 1H); 2.20–2.50 (m, 1H); 2.80 (m, 1H); 2.98–3.15 (m, 2H); 3.58 (d, 3H); 3.63 (d, 3H); 3.90 (d, 3H); 7.00–7.40 (m, 5H); 7.53 (dd, 1H); 8.30 (dd, 1H); 8.71 (d, 1H); 9.10 (bs, 1H).

EXAMPLE 12

Preparation of
N-(4-carboxy-2-pyridyl)-2-benzyl-3-hydroxymethoxyphosphinyl-propanamide (Compound 3)

A solution of N-(4-methoxycarbonyl-2-pyridyl)-2-benzyl-3-dimethoxyphosphiyl-propanamide (3.25 g; 0.008 moles), prepared as described in example 11, in NaOH 1N (20 ml) was kept at 60° C. for two hours.

After cooling and washing with ethyl acetate, the solution was acidified to pH about 2 with HCl 1N.

After 16 hours at room temperature, the precipitate was filtered and dried under vacuum at 50° C. affording N-(4-carboxy-2-pyridyl)-2-benzyl-3-hydroxymethoxyphosphinyl-propanamide (0.74 g; 23.6% yield) as white solid.

m.p. 226°–228° C.

Mass (Chemical ionization, CH$_2$N$_2$): 393

$^1$H-NMR (200 MHz, DMSO-d$_6$+D$_2$O): δ (ppm): 1.48–1.70 (m, 1H); 2.00–2.20 (m, 1H); 2.65–2.80 (m, 1H); 2.90–3.10 (m, 1H); 3.15–3.40 (m, 1H); 3.40 (d, 3H); 7.10–7.30 (m, 5H); 7.50 (dd, 1H); 8.45 (dd, 1H); 8.58 (bs, 1H).

EXAMPLE 13

Preparation of
N-(4-methoxycarbonyl-2-pyridyl)-2-benzyloxycarbonyl-amino-3-phenyl-propanamide A solution of N-benzyloxycarbonyl-L-phenylalanine (10 g; 0.034 moles) and carbonyldiimidazole (5.5 g; 0.034 moles) in anhydrous tetrahydrofuran (50 ml) was left at room temperature for 30 minutes. Methyl 2-amino-isonicotinate (5.2 g; 0.034 moles) was then added; the reaction mixture was kept at room temperature for 20 hours and then poured into water.

After extraction with ethyl acetate and drying on sodium sulphate, the solvent was evaporated to dryness.

The residue was purified by chromatography on silica gel (eluent CH$_2$Cl$_2$:CH$_3$OH=9:1) affording N-(4-methoxycarbonyl-2-pyridyl)-2-benzyloxycarbonylamino-3-propanamide (6.5; 45% yield) as oil.

$^1$H-NMR (200 MHz, CDCl$_3$): δ (ppm): 3.20 (m, 2H); 3.98 (s, 3H); 4.65 (m, 1H); 5.11 (dd, 2H); 7.10–7.40 (m, 10H); 7.62 (d, 1H); 8.38 (d, 1H); 8.72 (s, 1H).

EXAMPLE 14

Preparation of
N-(4-methoxycarbonyl-2-pyridyl)-2-amino-3-phenyl-propanamide

A solution of N-(4-methoxycarbonyl-2-pyridyl)-2-benzyloxycarbonyl-amino-3-phenyl-propanamide (5 g; 0.012 moles), prepared as described in example 13, in a mixture of ethyl acetate:methylene chloride=1:1 (200 ml) was hydrogenated at 2.7 arm and 22° C. in the presence of palladium on charcoal at 10% (450 mg).

After 72 hours, the catalyst was filtered off and the solution was evaporated to dryness under vacuum.

The crude was purified by chromatography on silica gel (eluent CH$_2$C$_2$:CH$_3$OH=95:5) affording N-(4-methoxycarbonyl-2-pyridyl)-2-amino-3-phenyl-propanamide (2.37 g; 69% yield) as white solid.

$^1$H-NMR (300 MHz, CDCl$_3$): δ (ppm): 1.62 (bs, 1H); 2.82 (dd, 1H); 3.40 (dd, 1H); 3.98 (s, 3H); 7.20–7.40 (m, 5H); 7.61 (dd, 1H); 8.43 (d, 5 1H); 8.82 (s, 1H).

Alternatively, by working in a way similar to that above reported and by hydrogenating N-(4-methoxycarbonyl-2-pyridyl)-2-henzyloxycarbonylamino-3-phenyl-propanamide (2.3 g; 0.0053 moles) in absolute ethanol (100 ml) and in the presence of hydrochloric acid 12N (0.44 ml; 0.0053 moles), N-(4-methoxycarbonyl-2-pyridyl)-2-amino-3-phenylpropanamide hydrochloride (1.58 g; 89% yield) was obtained.

EXAMPLE 15

Preparation of N-(4-methoxycarbonyl-2-pyridyl)-2-dibenzyloxyphosphinylamino-3-phenyl-propanamide Dibenzyl chlorophosphonate (0.0038 moles), freshly prepared from dibenzyl phosphite and NCS (N-chlorosuccinimide) in toluene, was added under nitrogen atmosphere and at room temperature to a solution of N-(4-methoxycarbonyl-2-pyridyl)-2-amino-3-phenyl-propanamide (1.65 g; 0.0055 moles), prepared as described in example 14, and triethylamine (0.53 ml; 0.0038 moles) in toluene (50 ml).

After 5 hours, the reaction mixture was poured into water and extracted with ethyl acetate (2×100 ml).

The organic phase was dried on sodium sulphate and the solvent evaporated under vacuum.

The residue was chromatographed on silica gel (eluent $CH_2Cl_2:CH_3OH=95:5$) affording N-(4-methoxycarbonyl-2-pyridyl)-2-dibenzyloxyphosphinylamino-3-phenyl-propanamide (1.5 g; 48.8% yield) as oil.

$^1$H-NMR (200 MHz, $CDCl_3$): δ (ppm): 3.08 (d, 2H); 3.63 (t, $D_2O$ exchange); 3.94 (s, 3H); 4.06–4.20 (m, 1H); 4.69 (dd, 1H); 4.88–5.00 (m, 3H); 7.10–7.30 (m, 15H); 7.55 (dd, 1H); 8.26 (dd, 1H); 8.67 (s, 1H); 9.13 (bs, $D_2O$ exchange).

EXAMPLE 16

Preparation of N-(4-carboxy-2-pyridyl)-2-dibenzyloxyphosphinylamino-3-phenyl-propanamide A suspension of N-(4-methoxycarbonyl-2-pyridyl)-2-dibenzyloxyphosphinyamino-3-phenyl-propanamide (1.5 g; 0.0027 moles), prepared as described in example 15, in NaOH 1N (10 ml) was treated with acetone (10 ml) and left at room temperature for 3 hours.

The pH value was brought to 3 with HCl 1N and the mixture was extracted with ethyl acetate (2×50 ml).

After drying on sodium sulphate, the solvent was evaporated under vacuum.

The residue was chromatographed on silica gel (eluent $CH_2Cl_2:CH_3OH: CH_3COOH=90:10:1$) affording N-(4-carboxy-2-pyridyl)-2-dibenzyloxyphosphinylamino-3-phenyl-propanamide (0.25 g; 17% yield) as oil.

$^1$H-NMR (200 MHz, DMSO-$d_6$+$D_2O$): δ (ppm): 2.78 (m, 1H); 3.08 (m, 1H); 4.15 (m, 1H); 4.25 (dd, 1H); 4.55–70 (m, 3H); 7.05–7.40 (m, 15H); 7.50 (dd, 1H); 8.36 (d, 1H); 8.50 (s, 1H).

EXAMPLE 17

Preparation of N-(4-carboxy-2-pyridyl)-3-phenyl-2-phosphonoamino-propanamide (Compound 4)

A solution of N-(4-carboxy-2-pyridyl)-2-dibenzyloxyphosphinylamino-3-phenyl-propanamide (3.8 g; 0.007 moles), prepared as described in example 16, in dimethylformamide (200 ml) was hydrogenated at 2.4 arm and 20° C. in the presence of palladium on charcoal at 10% (0.4 g).

After 2 hours, the catalyst was filtered off and the solvent evaporate under vacuum.

The crude product, which was solidified from methanol, afforded N-(4-carboxy-2-pyridyl)-3-phenyl-2-phosphonoamino-propanamide (0.58 g; 23% yield) as white solid.

m.p. 135°–137° C.

Mass (Chemical ionization): 408

$^1$H-NMR (200 MHz, DMSO-$d_6$+$D_2O$): δ (ppm): 3.10 (m, 2H); 4.35 (m, 1H); 7.23 (m, 5H); 7.53 (d, 1H); 8.44 (m, 2H).

EXAMPLE 18

Preparation of N-(2-ethoxycarbonyl-4-pyrrolyl)-3-phenyl-2-(tert-butoxycarbonyl)amino-propanamide N-hydroxysuccinimide (3.29 g; 28.6 mmoles) was added to a solution of N-tert-butoxycarbonyl-L-phenylalanine (6.89 g; 26 mmoles) in dioxane (10.5 ml), kept under nitrogen atmosphere.

A solution of dicyclohexylcarbodiimide (5.9 g; 28.6 mmoles) in dioxane (59 ml) was added dropwise at room temperature.

The reaction mixture was kept under stirring at room temperature and under nitrogen atmosphere for 3 hours.

The obtained precipitate was filtered off and a solution of 4-amino-2-ethoxycarbonyl-pyrrole (4 g; 26 mmoles) in dioxane (50 ml) was added therein.

The reaction mixture was kept under stirring at room temperature for 12 hours, then it was diluted with water (150 ml) and extracted with ethyl acetate (3×50 ml).

The collected organic phases were washed twice with water (50 ml), dried on sodium sulphate and evaporated to dryness under vacuum. The obtained oily residue was crystallized from ethyl acetate affording N-(2-ethoxycarbonyl-4-pyrrolyl)-3-phenyl-2-(tert-butoxycarbonyl)amino-propanamide (6.2 g; 59.5% yield).

m.p. 148°–151° C.

$^1$H-NMR (300 MHz, $CDCl_3$): δ (ppm): 1.32 (t, 3H); 1.40 (s, 9H); 3.10 (m, 2H); 4.29 (q, 2H); 4.49 (m, 1H); 5.18 (bs, 1H); 6.63 (t, 1H); 7.18–7.35 (m, 5H); 7.38 (s, 1H); 7.86 (bs, 1H); 9.13 (bs, 1H).

EXAMPLE 19

Preparation of N-(2-ethoxycarbonyl-4-pyrrolyl)-2-amino-3-phenyl-propanamide

N-(2-ethoxycarbonyl-4-pyrrolyl)-3-phenyl-2-(tert-butoxycarbonyl)amino-propanamide (4 g; 9.97 mmoles), prepared as described in example 18, was dissolved in trifluoroacetic acid (20 ml).

The reaction mixture was kept under stirring at room temperature for 30 minutes, then evaporated under vacuum.

The residue was diluted with water (30 ml) and sodium bicarbonate was added till basic pH.

After extraction with ethyl acetate (3×20 ml), the collected organic phases were washed twice with water, dried on sodium sulphate and evaporated to dryness under vacuum.

The obtained crude was collected with ligroin and filtered affording N-(2-ethoxycarbonyl-4-pyrrolyl)-2-amino-3-phenyl-propanamide (2.67 g; 89% yield) which was used in the subsequent reaction without further purification.

m.p. 139°–142° C.

EXAMPLE 20

Preparation of
N-(2-ethoxycarbonyl-4-pyrrolyl)-2-(n.propylphenoxyphosphinyphosphinyl)amino-3-phenyl-propanamide A solution of phenol (0.78 g; 8.3 mmoles) in anhydrous methylene chloride (13.5 ml) and triethylamine (1.16 ml; 8.3 mmoles) were added at 0° C. and under nitrogen atmosphere to a solution of n.propylphosphonic dichloride (1.34 g; 8.3 mmoles) in anhydrous methylene chloride (13.5 ml).

The reaction mixture was kept under stirring at room temperature for 3 hours.

At the end, a solution of N-(2-ethoxycarbonyl-4-pyrrolyl)-2-amino-3-phenyl-propanamide (2 g; 6.64 moles), prepared as described in example 19, in anhydrous methylene chloride (13.5 ml) and triethylamine (1.16 ml; 8.3 mmoles) was added dropwise at 0° C.

The reaction mixture was kept under stirring at room temperature and under nitrogen atmosphere for 12 hours.

The mixture was then diluted with water (30 ml) and the phases were separated.

The organic phase was dried on sodium sulphate and evaporated under vacuum obtaining a crude which, by chromatography on silica gel (eluent $CH_2Cl_2:CH_3OH=95:5$) and subsequent crystallization from ethyl acetate:ligroin=1:1 afforded N-(2-ethoxycarbonyl-4-pyrrolyl)-2-(n.-propylphenoxyphosphinyl)amino-3-phenyl-propanamide (1g; 31.2% yield).

m.p. 170°–173° C.

$^1$H-NMR (200 MHz, $CDCl_3$): δ (ppm): 0.87 (m, 3H); 1.31 (t, 3H); 1.37–1.69 (m, 4H); 2.90 (dd, 1H); 3.05 (dd, 1H); 4.16 (dd, 1H); 4.25 (q, 2H); 6.50 (m, 1H); 6.95–7.30 (m, 11H); 8.91 (bd, 1H); 9.20 (bs,1H).

EXAMPLE 21

Preparation of
N-(2-carboxy-4-pyrrolyl)-2-(hydroxy-n.propylphosphinyl)amino-3-phenyl-propanamide dilithium salt
(Compound 5)

A solution of lithium hydroxide hydrate (0.304 g; 7.25 moles) in water (1.8 ml) was added to a solution of N-(2-ethoxycarbonyl-4-pyrrolyl)-2-(n.propylphenoxyphosphinyl)amino-3-phenyl-propanamide (1 g; 0.00207 moles), prepared as described in example 20, in tetrahydrofuran (10 ml).

The reaction mixture was kept under starting at room temperature for 7 days.

At the end, it was diluted with water (10 ml) and extracted with ethyl acetate (3×10 ml).

The aqueous phase was evaporated under vacuum and collected a few times with ethyl acetate evaporating to dryness each time.

The obtained crude was crystallized from a mixture of ethyl acetate:ethanol=1:1, affording N-(2-carboxy-4-pyrrolyl)-2-(hydroxy-n.propylphosphinyl)amino-3-phenyl-propanamide dilithium salt (0.7 g; 86.4% yield).

m.p. 270° C. (dec.)

$^1$H-NMR (200 MHz, $D_2O$): δ (ppm): 0.63 (m, 3H); 1.11 (m, 2H); 1.15 (m, 2H); 2.87 (d, 2H); 3.75 (dd, 1H); 6.34 (d, 1H); 6.87 (t, 1H); 7.05–7.24 (m, 5H).

EXAMPLE 22

Preparation of N-(4-ethoxycarbonylmethyl-2-thiazolyl)-2-(n.propylphenoxyphosphinyl)amino-3-phenyl-propanamide By working in a way similar to that described in example 20 and by using N-(4-ethoxycarbonylmethyl-2-thiazolyl)-2-amino-3-phenyl-propanamide (1.5 g; 0.0045 moles), prepared as described in example 2, a crude product was obtained which, chromatographed on silica gel (eluent ethyl acetate), afforded N-(4-ethoxycarbonylmethyl-2-thiazolyl)-2-(n.propylphenoxyphosphinyl)amino-3-phenyl-propanamide (0.44 g; 19% yield).

m.p. 95°–100° C.

$^1$H-NMR (200 MHz, $CDCl_3$): δ (ppm): 0.87 (m, 3H); 1.25 (t, 3H); 1.35–1.61 (m, 4H); 2.86 (m, 1H); 3.11 (m, 1H); 3.64 (s, 2H); 4.15 (q, 2H); 4.38–4.57 (m, 1H); 6.78 (d, 1H); 8.90–7.25 (m, 11H); 10.92 (d, 1H).

EXAMPLE 23

Preparation of
N-(4-carboxymethyl-2-thiazolyl)-2-(hydroxy-n.propylphosphinyl)amino-3-phenyl-propanamide dilithium salt
(Compound 6)

By working in a way similar to that described in example 21 and by using N-(4-ethoxycarbonylmethyl-2-thiazolyl)-2-(n.propylphenoxyphosphinyl)amino-3-phenyl-propanamide (0.9 g; 0.00175 moles), prepared as described in example 22, and lithium hydroxide hydrate (0.158 g; 0.00376 moles) a crude was obtained which, crystallized from ethyl acetate:ethanol=2:1, afforded N-(4-carboxymethyl-2-thiazolyl)-2-(hydroxy-n.propylphosphinyl)amino-3-phenyl-propanamide dilithium salt (0.5 g; 67.57% yield).

m.p. 270° C. (dec.) Mass (chemical ionization, $CH_2N_2$): 440

$^1$H-NMR (200 MHz, $D_2O$): δ (ppm): 0.59 (bt, 3H); 1.01–1.18 (m, 4H); 2.90 (dd, 2H); 3.34 (s, 2H); 3.88–4.01 (m, 1H); 6.68 (s, 1H); 7.04–7.22 (m, 5H).

EXAMPLE 24

Preparation of
N-(4-ethoxycarbonylmethyl-2-thiazolyl)-3-(4-fluorophenyl)-2-(tert-butoxycarbonyl)amino-propane By working in a way similar to that described in example 18 and by using N-tert-butoxycarbonyl-L-4-fluorophenylalanine (1 g; 0.0035 moles) and ethyl (2-amino-4-thiazolyl)acetate (0.65 g; 0.0035 moles), a crude was obtained which, chromatographed on silica gel (eluent ligroin:ethyl acetate=1:1), afforded N-(4-ethoxycarbonylmethyl-2-thiazolyl)-3-(4-fluorophenyl)-2-(tert-butoxycarbonyl)aminopropanamide $^1$H-NMR (200 MHz, $CDCl_3$): δ (ppm): 1.24 (t, 3H); 1.38 (s, 9H); 3.06 (dd, 1H); 3.23 (dd, 1H); 3.65 (s, 2H); 4.18 (q, 2H); 4.51–4.64 (m, 1H); 4.79 (d, 1H); 6.81 (s, 1H); 6.92–7.18 (m, 4H); 9.42 (s, 1H).

EXAMPLE 25

Preparation of
N-(4-ethoxycarbonylmethyl-2-thiazolyl)-2-amino-3-(4-fluorophenyl)-propanamide By working in a way similar to that described in example 19 and by
using N-(4-ethoxycarbonylmethyl-2-thiazolyl)-3-(4-fluorophenyl)-2-(tert-butoxycarbonyl)amino-propanamide (0.77 g; 0.0017 moles), prepared as described in example 24, N-(4-ethoxycarbonylmethyl-2-thiazolyl)-2-amino-3-(4-fluorophenyl)-propanamide (0.59 g; 98.5% yield) was obtained.

m.p. 124°–127° C.

EXAMPLE 26

Preparation of
N-(4-ethoxycarbonylmethyl-2-thiazolyl)--3-(4-fluorophenyl)-2-(n.propylphenoxyphosphinyl)amino-propanamide By working in a way similar to that described in example 20 and by using phenol (0.401 g; 4.27 mmoles), triethylamine (0.595 ml; 4.27 mmoles), n.propylphosphonic dichloride (0.687 g; 4.27 mmoles) and N-(4-ethoxycarbonylmethyl-2-thiazolyl)-2-amino-3-(4-fluorophenyl)propanamide (1 g; 2.85 mmoles), prepared as described in example 25, N-(4-ethoxycarbonylmethyl-2-thiazolyl)-3-(4-fluorophenyl)-2-(n.propylphenoxyphosphiyl)amido-propanamide (1.5 g; 66% yield) as dense oil was obtained.

$^1$H-NMR (200 MHz, CDCl$_3$): Δ (ppm): 1.08 (t, 3H); 1.24 (t, 3H); 1.73-2.24 (m, 4H); 3.07 (dd, 1H); 3.19 (dd, 1H); 3.66 (s, 2H); 4.15 (q, 2H); 4.89 (dd, 1H); 6.78-7.35 (m, 11H).

EXAMPLE 27 preparation of
N-(4-carboxymethyl-2-thiazolyl)-3-(4-fluorophenyl)-2-(hydroxy-n.propylphosphinyl)amino-propanamide dilithium salt (Compound 7)

By working in a way similar to that described in example 21 and by using N-(4-ethoxycarbonylmethyl-2-thiazolyl)-3-(4-fluorophenyl)-2-(n.propylphenoxyphosphinyl)amino-propanamide (0.68 g; 1.27 mmoles), prepared as described in example 26, a crude was obtained which, collected with ethanol and filtered, afforded N-(4-carboxymethyl-2-thiazolyl)-3-(4-fluorophenyl)-2-(hydroxy-n.propylphosphinyl)amino-propanamide dilithium salt (0.44 g; 78.6 yield).

m.p. 230° C. (dec.)

$^1$H-NMR (200 MHz, D$_2$O): δ (ppm): 0.58 (m, 3H); 0.92-1.12 (m, 4H); 2.79 (dd, 1H); 2.91 (dd, 1H); 3.34 (s, 2H); 3.88 (dd, 1H); 6.66 (s, 1H); 6.78-6.91 (m, 2H); 7.01-7.12 (m, 2H).

EXAMPLE 28

Preparation of
N-(2-ethoxycarbonyl-4-pyrrolyl)-2-(tert-butoxycarbonyl)amino-3-(4-thiazolyl)-propanamide By working in a way similar to that described in example 18 and by using N-tert-butoxycarbonyl-L-3-(4-thiazolyl)alanine (1 g; 3.67 mmoles) and 4-amino-2-ethoxycarbonyl-pyrrole (0.566 g; 3.67 mmoles), N-(2-ethoxycarbonyl-4-pyrrolyl)-2-(tert-butoxycarbonyl)amino-3-(4-thiazolyl)-propanamide (1.4 g; 93.4% yield) was obtained.

m.p. 217°-220° C.

$^1$H-NMR (200 MHz, DMSO-d$_6$): δ (ppm): 1.27 (t, 3H); 1.32 (s, 9H); 2.95-3.21 (m, 2H); 4.20 (q, 2H); 4.32-4.45 (m, 1H); 6.73 (t, 1H); 7.40 (d, 1H); 7.19 (s, 1H); 7.33 (s, 1H); 9.30 (s, 1H); 9.98 (s, 1H); 11.61 (s, 1H).

EXAMPLE 29

Preparation of
N-(2-ethoxycarboyl-4-pyprrolyl)-2-amino-3-(4-thiazololyl)-propanamide working in a way similar to that described in example 19 and by using N-(2-ethoxycapbonyl-4-pyrrolyl)-2-(tert-butoxycarbonyl)amino-3-(4-thiazolyl)-propanamide (1.48 g; 0.0037 moles), prepared as described in example 28, N-(2-ethoxycarbonyl-4-pyrrolyl)-2-amino-3-(4-thiazolyl)-propanamide (1.0; 87.7% yield) as oil was obtained.

$^1$H-NMR (200 MHz, CDCl$_3$): δ (ppm): 1.31 (t, 3H); 3.12 (dd, 1H); 3.42
1H); (dd, 1H); 3.83 (dd, 1H); 4.28 (q, 2H); 6.73 (t, 1H); 7.10 (d, 7.50 (t, 1H); 8.75 (t, 1H); 9.18 (bs, 1H); 9.37 (s, 1H).

EXAMPLE 30

Preparation of
N-(2-ethoxycarbonyl-4-pyprolyl)-2-(n.propylphenoxyphosphinyl)amino-3-(4-thiazolyl)-propanamide By working in a way similar to that described in example 26 and by using N-(2-ethoxycarbonyl-4-pyrrolyl)-2-amino-3-(4-thiazolyl)propanamide (0.8 g; 2.59 mmoles), prepared as described in example 29, N-(2-ethoxycarbonyl-4-pyrrolyl)-2-(n.propylphenoxyphosphinyl)amino-3-(4-thiazolyl)-propanamide (0.45 g; 35.5% yield) was obtained. m.p. 175°-178° C.

$^1$H-NMR (300 MHz, DMSO-d$_6$): δ (ppm): 0.83 (t, 3H); 1.28 (t, 3H); 1.33-1.76 (m, 4H); 2.96 (dd, 2H); 3.12 (dd, 1H); 4.11 (q, 2H);
1H); 5.32-5.59 (m, 1H); 6.60 (t, 1H); 6.90-7.27 (m, 6H); 7.38 (m, 9.01 (m, 1H).

EXAMPLE 31

Preparation of
N-(2-Carboxy-4-pyrrolyl)-2-(hydroxy-n.propylphosphinyl)amino-3-(4-thiazolyl)-propanamide dilithium salt (Compound 8)

By working in a way similar to that described in example 21 and by using N-(2-ethoxycarbonyl-4-pyrrolyl)-2-(n.propylphenoxyphosphinyl)-amino-3-(4-thiazolyl)-propanamide (0.42 g; 0.86 mmoles), prepared as described in example 30, a crude was obtained which, collected with ethanol:water=1:1, afforded N-(2-carboxy-4-pyrrolyl)-2-(hydroxy-n.propylphosphinyl)amino-3-(4-thiazolyl)propanamide dilithium salt (0.3 g; 89.6% yield).

m.p. 270° C. (dec.)

Mass (Chemical ionization, isobutane): m/e 413 (M-1)

$^1$H-NMR (300 MHz, D$_2$O): δ (ppm): 0.78 (t, 3H); 1.07-1.20 (m, 4H); 3.00-3.12 (m, 2H); 3.82-3.92 (dd, 1H); 6.41 (s, 1H); 6.92 (m, 1H); 7.21 (m, 1H); 8.79 (m, 1H).

Example 32

Preparation of
N-(4-ethoxycarbonylmethyl-2-thiazolyl)-2-(tert-butoxycarbonyl)amino-3-(2-thienyl)-propanamide By working in a way similar to that described in example 18 and by using N-tert-butoxycarbonyl-L-3-(2-thienyl)alanine (2 g; 7.4 mmoles) and ethyl (2-amino-4-thiazolyl)acetate (1.38 g; 7.4 mmoles), a crude was obtained which, chromatographed on silica gel (eluent ligroin:ethyl acetate=6:4), afforded N-(4-ethoxycarbonylmethyl-2-thiazolyl)-2-(tert-butoxycarbonyl)amino-3-(2-thiazolyl)acetate (2.1 g; 65% yield) as oil.

$^1$H-NMR (200 MHz, CDCl$_3$): δ (ppm): 1.26 (t, 3H); 1.42 (s, 9H); 3.42 (dd, 2H); 3.68 (s, 2H); 4.17 (q, 2H); 4.54-4.69 (m, 1H); 4.93 (d, 1H); 6.70-6.95 (m, 3H); 7.18 (dd, 1H); 9.51 (bs, 1H).

EXAMPLE 33

Preparation of N-(4-ethoxycarbonylmethyl-2-thiazolyl)-2-amino-3-(2-thienyl)-propanamide By working in a way similar to that described in example 19 and by using N-(4-ethoxycarbonylmethyl-2-thiazolyl)-2-(tert-butoxycarbonyl)amino-3-(2-thienyl)-propanamide (2.1 g; 0.0048 moles), prepared as described in example 32, N-(4-ethoxycarbonylmethyl-2-thiazolyl)-2-amino-3-(2-thienyl)propanamide (1.6 g; 98% yield) was obtained.

m.p. 98°–102° C.

$^1$H-NMR (200 MHz, CDCl$_3$): δ (ppm): 1.25 (t, 3H); 3.22 (dd, 1H); 3.47 1H); 4.16 (q, 2H); 6.80 (s, 1H); (dd, 1H); 3.69 (s, 2H); 3.86 (dd, 6.85–6.97 (m, 3H); 7.18 (dd, 1H).

EXAMPLE 34

Preparation of N-(4-ethoxycarboylmethyl-2-thiazolyl)-2-(n.propylphenoxyphosphinyl)amino-3-(2-thienyl)-propanamide By working in a way similar to that described in example 20 and by using phenol (0.85 g; 0.009 moles), triethylamine (0.9 g; 0.009 moles), n.propylphosphonic dichloride (1.5 g; 0.0093 moles) and N-(4-ethoxycarbonylmethyl-2-thiazolyl)-2-amino-3-(2-thienyl)-propanamide (1.6 g; 0.0048 moles), prepared as described in example 33, N-(4-ethoxycarbonylmethyl-2-thiazolyl)-2-(n.propylphenoxyphosphinyl)amino-3-(2-thienyl)-propanamide (0.65 g; 26% yield) was obtained as oil.

$^1$H-NMR (200 MHz, CDCl$_3$): δ (ppm): 0.93 (t, 3H); 1.22 (t, 3H); 1.48–1.88 (m, 4H); 3.16 (dd, 2H); 3.67 (s, 2H); 4.14 (q, 2H); 4.23–4.49 (m, 1H); 6.72–7.25 (m, 10H); 10.84–11.22 (bs, 1H).

EXAMPLE 35

Preparation of N-(4-carboxymethyl-2-thiazolyl)-2-(hydroxy-n.propylphosphinyl)amino-3-(2-thienyl)-propanamide dilithium salt (Compound 9)

By working in a way similar to that described in example 21 and by using N-4-ethoxycarbonylmethyl-2-thiazolyl)-2-(n.propylphenoxyphosphinyl)amino-3-(2-thienyl)-propanamide (0.8 g; 0.0015 moles), prepared as described in example 34, a crude was obtained which, crystallized from ethanol, afforded N-(4-carboxymethyl-2-thiazolyl)-2-(hydroxy-n.propylphosphinyl)amino-3-(2-thienyl)propanamide dilithium salt (0.220 g; 34% yield).

m.p. 230° C. (dec.)

$^1$H-NMR (200 MHz, DMSO-d$_6$+D$_2$O): δ (ppm): 0.71 (bt, 3H); 1.02–1.22 (m, H) 3.0 (dd, 1H); 3.29 (dd, 1H); 3.52 (s, 2H); 3.87 (m, 1H); 6.89 (m, 3H); 7.27 (t, 1H).

EXAMPLE 36

Preparation of N-(4-ethoxycarbonylmethyl2-thiazolyl)-2-(hydroxy-n.-propylphosphinyl)amino-3-phenyl-propanamide sodium salt (Compound 10)

A solution of sodium bicarbonate (0.105 g; 1.26 mmoles) in water (6.5 ml) was added to a solution of N-(4-ethoxycarbonylmethyl-2-thiazolyl)-2-(n.propylphenoxyphosphinyl)amino-3-phenyl-propanamide (0.65 g; 0.00126 moles) in tetrahydrofuran (13 ml), prepared as described in example 22, kept under stirring at room temperature.

After 1 hour the reaction mixture was diluted with water (25 ml) and the phases were separated.

The aqueous phase was washed with ethyl ether (3×20 ml) and evaporated to dryness under vacuum.

The residue was then collected with ethanol and evaporated again under vacuum.

The solid thus obtained was collected with acetone and filtered, affording N-(4-ethoxycarbonylmethyl-2-thiazolyl)-2-(hydroxy-n.propylphosphinyl)amino-3-phenyl-propanamide sodium salt (0.5 g; 86% yield).

m.p. 180° C. (slow dec.)

$^1$H-NMR (200 MHz, D$_2$O): δ (ppm): 0.59 (m, 3H); 1.06–1.18 (m, 1.60 (t, 3H); 2.90 (dd, 2H); 3.58 (s, 2H); 3.86–3.99 (m, 1H); 4.01 (q, 2H); 6.70 (s, 1H); 7.03–7.20 (m, 5H).

EXAMPLE 37

Preparation of N-(4-carboxymethyl-2-thiazolyl)-3-phenyl-2-(tert-butoxycarbonyl)amino-propanamide A solution of NaOH 10.8 N (1.57 ml; 16.97 mmoles) was added to a suspension of N-(4-ethoxycarbonylmethyl-2-thiazolyl)-3-phenyl-2-(tert-butoxycarbonyl)amino-propanamide (3.5 g; 0.08 mmoles), prepared as described in example 1, in a mixture of ethanol (35 ml) and water (5 ml), kept under stirring and under nitrogen atmosphere. After 12 hours the reaction mixture was diluted with water (100 ml), acidified with potassium bisulphate and extracted with ethyl acetate (100 ml).

The organic phase was dried on sodium sulphate and evaporated to dryness under vacuum.

The obtained residue was collected with ethyl ether:-ligroin=1:1 (50 ml) and filtered affording N-(4-carboxymethyl-2-thiazolyl)-3-phenyl-2-(tert-butoxycarbonyl)amino-propanamide (3.13 g; 95% yield).

m.p. 189°–190° C.

$^1$H-NMR (200 MHz, DMSO-d$_6$): δ (ppm): 1.31 (s, 9H); 2.68 (dd, 1H); 3.0 (dd, 1H); 3.60 (s, 2H); 4.30–4.47 (m, 1H); 6.95 (s, 1H); 7.15–7.37 (m, 5H).

EXAMPLE 38

Preparation of N-(4-dimethylaminocarbonylmethyl-2-thiazolyl)-3-phenyl-2-2-(tert-butoxycarbonyl)amino-propanamide N-hydroxysuccinimide (0.968 g; 8.41 mmoles) and dicyelohexylcarbodiimide (1.89 g; 9.17 mmoles) were added to a solution of N-(4-carboxymethyl-2-thiazolyl)3-phenyl-2-(tert-butoxycarbonyl)amino-propanamide (3.1 g; 7.46 mmoles), prepared as described in example 37, in dioxane (60 ml).

After 4 hours the formed precipitate was filtered off and dimethylamine (2.13 ml; 16.81 mmoles) was added.

After 12 hours the mixture was diluted with ethyl acetate (30 ml); the organic phase was washed with water (30 ml), dried on sodium sulphate and evaporated to dryness under vacuum.

The obtained crude was chromatographed on silica gel (eluent ethyl acetate) and the recovered product was collected with ligroin and filtered affording N-(4-dimethylaminocarbonylmethyl-2-thiazolyl)-3-phenyl-2-(tert-butoxycarbonyl)amino-propanamide (2.7 g; 82% yield).

m.p. 139°–140° C.

$^1$H-NMR (200 MHz, CDCl$_3$): δ (ppm): 1.36 (s, 9H); 2.97 (s, 3H); 3.04 (s, 3H); 2.97–3.12 (dd, 1H); 3.18–3.20

(dd, 1H); 3.73 (s, 2H); 4.52–4.68 (m, 1H); 4.90–5.01 (m, 1H); 6.75 (s, 1H); 7.12–7.33 (m, 5H); 9.63–9.88 (m, 1H).

EXAMPLE 39

Preparation of N-(4-dimethylamiocarbonylmethyl-2-thiazolyl)-2-amino-3-phenyl-propanamide A solution of N-(4-dimethylaminocarbonylmethyl-2-thiazolyl)-3-phenyl-3-phenyl-propanamide (2.65 g; 6.13 mmoles), prepared as described in example 38, in trifluoroacetic acid (20 ml) was left under stirring at room temperature for 30 minutes.

The solvent was evaporated under vacuum and the residue was collected with water (20 ml), treated with sodium carbonate till basic pH, saturated with sodium chloride and extracted with methylene chloride (3×30 ml).

The organic phase was washed with brine, dried on sodium sulphate and evaporated to dryness.

The obtained residue was collected with ethyl ether (30 ml) and filtered affording N-(4-dimethylaminocarbonylmethyl-2-thiazolyl)-2-amino-3-phenyl-propanamide (1.7 g; 83% yield).

m.p. 103°–104° C.

$^1$H-NMR (200 MHz, CDCl$_3$): δ (ppm): 2.70–2.82 (dd, 1H); 2.95 (s, 3H); 3.05 (s, 3H); 3.30–3.40 (dd, 1H); 3.73 (s, 2H); 3.76–3.83 (dd, 1H); 6.75 (s, 1H); 7.15–7.37 (m, 5H).

EXAMPLE 40

Preparation of N-(4-dimethylaminocarbonylmethyl-2-thiazolyl)-2-(n.propylphenoxyphosphinyl)amino-3-phenyl-propanamide By working in a way similar to that described in example 26 and by using N-(4-dimethylaminocarbonylmethyl-2-thiazolyl)-2-amino-3-phenyl-propanamide (1.68 g; 5.05 mmoles), prepared as described in example 39, a crude N-(4-dimethylaminocarbonylmethyl-2-thiazolyl)-2-(n.propylphenoxyphosphinyl)amino-3-phenyl-propanamide, which was used as such in the subsequent reaction step, was obtained.

EXAMPLE 41

Preparation of N-(4-dimethylaminocarbonylmethyl-2-thiazolyl)-2-hydroxy-n.propylphosphinyl)amino-3-phenyl-propanamide sodium salt (Compound 11)

By working in a way similar to that described in example 36 and by using N-(4-dimethylaminocarbonylmethyl-2-thiazolyl)-2-(n.propylphenoxyphosphinyl)amino-3-phenyl-propanamide (2.6 g; 5.05 moles), prepared as described in example 40, N-(4-dimethylaminocarbonylmethyl-2-thiazolyl)-2-(hydroxy-n.propylphosphinyl)amino-3-phenyl-propanamide sodium salt (0.52 g; 22% yield) was obtained.

m.p. 138°–143° C.

$^1$H-NMR (200 MHz, D$_2$O): δ (ppm): 0.52–0.62 (m, 3H); 0.98–1.14 (m, 4H); 2.75 (s, 3H); 2.80–2.90 (dd, 1H); 2.91 (s, 3H); 2.91–3.0 (dd, 1H); 3.62 (s, 2H); 3.86–3.98 (m, 1H); 6.72 (s, 1H); 7.04–7.20 (m, 5H).

EXAMPLE 42

Preparation of N-(2-ethoxycarbonyl-4-pyrrolyl)-3-(3,4-dichlorophenyl)-2-(tert-butoxycarbonyl)amino-propanamide By working in a way similar to that described in example 18 and by using N-tert-butoxycarbonyl-L-3-(3,4-dichlorophenyl)alanine (2 g; 5.98 moles) and 4-amino-2-ethoxycarbonyl-pyrrole (0.922 g; 5.98 mmoles), a crude was obtained which, chromatographed on silica gel (eluent ethyl acetate:ligroin=1:1 ) and further collected with ethyl ether:ligroin=1:1 and filtered, afforded N-(2-ethoxycarbonyl-4-pyrrolyl)-3-(3,4-dichlorophenyl)-2-(tert-butoxycarbonyl)amino-propanamide (2.3 g; 82% yield).

m.p. 175°–185° C.

$^1$H-NMR (200 MHz, DMOS-d$_6$+D$_2$O): δ (ppm): 1.13–1.29 (m, 12H); 2.68–2.82 (bdd, 1H); 2.92–3.02 (dd, 1H); 4.13–4.25 (q+m, 3H); 6.72 (t, 1H); 7.20–7.28 (m, 2H); 7.47–7.53 (m, 2H).

EXAMPLE 43

Preparation of N-(2-ethoxycarbonyl-2-pyrrolyl)-2-amino-3-(3,4-dichlorophenyl)-propanamide By working in a way similar to that described in example 19 and by using N-(2-ethoxycarbonyl-4-pyrrolyl)-3-(3,4-dichlorophenyl)-2-(tert-butoxycarbonyl)amino-propanamide (2.3 g; 4.89 mmoles), prepared as described in example 42, a etude was obtained which, collected with ethyl ether:ligroin=1:1 and filtered, afforded N-(2-ethoxycarbonyl-4-pyrrolyl)-2-amino-3-(3,4-dichlorophenyl)-propanamide (1.69 g; 93% yield).

m.p. 134°–136° C.

$^1$H-NMR (200 MHz, DMSO-d$_6$): δ (ppm): 1.27 (t, 3H); 2.63–2.75 (dd, 1H); 2.90–3.30 (dd, 1H); 3.48 (m, 1H); 4.22 (q, 2H); 6.76 (s, 1H); 7.17–7.84 (m, 2H); 7.49–7.54 (m, 2H); 9.76–9.91 (bs, 1H); 11.61 (bs, 1H).

EXAMPLE 44

Preparation of N-(2-ethoxycarbonyl-4-pyrrolyl)-3-(3,4-dichlorophenyl)-2-(n.propylphenoxyphosphinyl)amino-propanamide By working in a way similar to that described in example 26 and by using N-(2-ethoxycarbonyl-4-pyrrolyl)-2-amino-3-(3,4-dichlorophenyl)-propanamide (1.67 g; 4.51 mmoles), prepared as described in example 43, N-(2-ethoxycarbonyl-4-pyrrolyl)-3-(3,4-dichlorophenyl)-2-(n.propylphenoxyphosphinyl)amino-propanamide (1.6 g; 64% yield) was obtained.

m.p. 175°–177° C.

$^1$H-NMR (200 MHz, DMSO-d$_6$): δ (ppm): 0.78–0.88 (m, 3H); 1.20–1.60 (m, 4H); 1.27 (t, 3H); 2.58–2.78 (dd, 1H); 2.82–3.60 (dd, 1H); 3.92–4.10 (m, 1H); 4.17–4.27 (m, 2H); 5.31–5.58 (m, 1H); 6.61–6;78 (m, 1H); 6.87–7.24 (m, 7H); 7.40–7.57 (m, 2H); 9.97 (d, 1H).

EXAMPLE 45

Preparation of N-(2-carboxy-4-pyrrolyl)-3-(3,4-dichlorophenyl)-2-(hydroxy-n.propylphosphinyl)amino-propanamide dilithium salt (Compound 12)

By working in a way similar to that described in example 21 and by using N-(2-ethoxycarbonyl-4-pyrrolyl)-3-(3,4-dichlorophenyl)-2-(n.propylphenoxyphosphinyl)amino-propanamide (1.6 g; 2.9 mmoles), prepared as described in example 44, N-(2-carboxy-4-pyrrolyl)-3-(3,4-dichlorophenyl)-2-(hydroxy-n.propylphosphinyl)amino-propanamide dilithium salt (0.8 g; 60% yield) was obtained.

m.p. >300° C.

Mass (Chemical ionization): 476 (M+H)

$^1$H-NMR (200 MHZ, D$_2$O): δ (ppm): 0.60–0.68 (m, 3H); 0.97–1.16 (m, 4H); 2.85 (m, 2H); 3.75 (dd, 1H); 6.42 (d, 1H); 6.91 (d, 1H); 7.02–7.08 (m, 1H); 7.29–7.37 (m, 2H).

EXAMPLE 46

Preparation of N-(2-ethoxycarbonyl-4-pyrrolyl)-3-(4-biphenyl)-2-(tert-butoxycarbonyl)amino-propanamide By working in a way similar to that described in example 18 and by using N-tert-butoxycarbonyl-L-3-(4-biphenyl)alanine (2 g; 5.86 mmoles) and 4-amino-2-ethoxycarbonyl-pyrrole (0,903 g; 5.86 mmoles), N-(2-ethoxycarbonyl-4-pyrrolyl)-3-(4-biphenyl)-2-(tert-butoxycarbonyl)amino-propanamide (1.77 g; 63% yield) was obtained.

$^1$H-NMR (200 MHz, DMSO-d$_6$): δ (ppm): 1.23 (t, 3H); 1.30 (s, 9H); 2.85 (dd, 1H); 3.01 (dd, 1H); 4.22 (q, 2H); 4.20–4.32 (m, 1H); 5.58 (d, 1H); 6.74 (t, 1H); 7.07–7.67 (m, 10H); 10.02 (s, 1H); 11.65 (s, 1H).

EXAMPLE 47

Preparation of N-(2-ethoxycarbonyl-4-pyrrolyl)-2-amino-3-(4-biphenyl)-propanamide By working in a way similar to that described in example 19 and by using N-(2-ethoxycarbonyl-4-pyrrolyl)-3-(4-biphenyl)-2-(tert-butoxycarbonyl)amino-propanamide (2.15 g; 4.55 mmoles), prepared as described in example 46, N-(2-ethoxycarbonyl-4-pyrrolyl)-2-amino-3-(4-biphenyl)-propanamide (1.33 g; 77.5% yield) was obtained.

m.p. 15°–155° C.

$^1$H-NMR (200 MHz, DMS-d$_6$): δ (ppm): 1.26 (t, 3H); 2.72 (dd, 1H); 3.20 (dd, 1H); 3.51 (dd, 1H); 4.20 (q, 2H); 6.78 (t, 1H); 7.22–7.76 (m, 10H); 11.60 (bs, 2H).

EXAMPLE 48

Preparation of N-(2-ethoxycarbonyl-4-pyrrolyl)-3-(4-biphenyl)-2-(n.propylphenoxyphosphinyl)amino-propanamide By working in a way similar to that described in example 20 and by using N-(2-ethoxycarbonyl-4-pyrrolyl),-2-amino-3-(4-biphenyl)-propanamide (1.3 g; 3.44 mmoles), prepared as described in example 47, N-(2-ethoxycarbonyl-4-pyrrolyl)-3-(4-biphenyl)-2-(n.propyl-phenoxyphosphinyl)amino-propanamide (1.2 g; 62% yield) was obtained.

m.p. 180°–183° C.

$^1$H-NMR (200 MHz, CDCl$_3$): δ (ppm): 0.88 (t, 3H); 1.29 (t, 3H); 1.38–1.61 (m, 4H); 2.85–3.18 (m, 2H); 3.41–3.58 (t, 1H); 4.16–4.35 (m, 3H); 6.52 (t, 1H); 6.97–7.52 (m, 15H); 8.30 (bd, 1H); 8.98 (bs, 1H).

EXAMPLE 49

Preparation of N-(2-carboxy-4-pyrrolyl)-3-(4-biphenyl)-2-(hydroxy-n.propylphosphinyl)amino-propanamide dilithium salt (Compound 13)

By working in a way similar to that described in example 21 and by using N-(2-ethoxycarbonyl-4-pyrrolyl)-3-.(4-biphenyl)-2-(n.propylphenoxyphosphinyl)amino-propanamide (1.2 g; 2.14 mmoles), prepared as described in example 48, a etude was obtained which, collected with ethanol and filtered, afforded N-(2-carboxy-4-pyrrolyl)-3-(4-biphenyl)-2-(hydroxy-n.propylphosphinyl)amino-propanamide dilithium salt (0.860 g; 86% yield).

m.p. >300° C.

$^1$H-NMR (200 MHz, D$_2$O): δ (ppm): 0.58 (t, 3H); 0.99–1.17 (m, 4H); 2.88 (dd, 1H); 3.01 (dd, 1H); 3.81 (dd, 1H); 6.42 (d, 1H); 6.92 (d, 1H); 7.22–7.41 (m, 5H); 7.49–7.59 (m,

EXAMPLE 50

Preparation of N-(4-methoxycarbonyl-2-pyridyl)-2-(n.propylphenoxyphosphinyl)amino-3-phenyl-propanamide By working in a way similar to that described in example 20 and by using N-(4-methoxycarbonyl-2-pyridyl)-2-amino-3-phenyl-propanamide hydrochloride (1.55 g; 4.61 mmoles), prepared as described in example 14, a crude was obtained which, chromatographed on silica gel (eluent ethyl acetate:ligroin=6:4), afforded N-(4-methoxycarbonyl-2-pyridyl)-2-(n.propylphenoxyphosphinyl)amino-3-phenyl-propanamide (0.48 g; 21% yield).

$^1$H-NMR (200 MHz, CDCl$_3$): δ (ppm): 0.88 (m, 3H); 1.60 (m, 4H)i 3.08 (m, 2H); 3.94 (s, 3H); 4.26 ' (m, 1H); 6.90–7.30 (m, 10H); 7.56 (dd, 1H); 8.31 (dd, 1H); 8.60 (d, 1H).

EXAMPLE 51

Preparation of N-(4-carboxy-2-pyridyl)-2-(hydroxy-n.propylphosphinyl)amino-3-phenyl! -propanamide dilithium salt (Compound 14)

By working in a way similar to that described in example 21 and by using N-(4-methoxycarbonyl-2-pyridyl)-2-(n.propylphenoxyphosphinyl)amino-3-phenyl-propanamide (0.46 g; 0.955 mmoles), prepared as described in example 50, a crude was obtained which, collected with a mixture of ethanol:diethyl ether=1:3 (10 ml) and filtered, afforded N-(4-carboxy-2-pyridyl)-2-(hydroxy-n.propylphosphinyl)amino-3-phenyl-propanamide dilithium salt (0.32 gl 83% yield).

m.p. 250° C. (slow dec.)

$^1$H-NMR (200 MHz, D$_2$O): δ (ppm): 0.60 (m, 3H); 1.10 (m, 4H); 2.96 (m, 2H); 3.88 (q, 1H); 7.18 (m, 5H); 7.36 (dd, 1H); 7.83 (s, 1H); 8.29 (d, 1H).

EXAMPLE 52 pharmacological activity a) In vitro ECE-inhibitory activity

The ECE-inhibitory activity in vitro was evaluated according to the method reported in the literature by M. Auger et al., Eur. J. Pharmacol., 224, (1992), 101–102.

Male New Zealand rabbits (2.5-3 Kg) were sacrificed with an excess of pentobarbital and blood was drawn. The left saphenous artery was removed and cleaned of the surrounding tissue, cut into 2-3 mm length rings and suspended in 25 ml baths containing Krebs-Henseleit solution at 370° C. and oxygenated with $O_2$ containing 5% $CO_2$. This solution was composed of (mM); NaCl, 118; KCl, 4.7; $CaCl_2$, 2.5; $KH_2PO_4$, 1.2; $MgSO_4$, 1.2; $NaHCO_3$, 2.5; glucose, 11. The preparations were kept under tension and readjusted to 1 g during the equilibration period (1 hour).

After said period, the preparations were exposed to a submaximal concentration of norepinephrine 1 μM which was repeated every 30 minutes until the response was stable. A concentration of acetylcholine 10 μM on the contraction of norepinephrine verified the presence of the endothelium.

After 30 minutes from the last contraction due to norepinephrine, a concentration of human Big endothelin $3\times10^{-8}M$ was administered. After reaching the plateau the preparations were washed for 30 minutes and a concentration 1 μM of the compound to be tested or of its carrier was administered keeping them in contact for 30 minutes, after that a concentration of Big endothelin $3\times10^{-8}M$ was administered again. The percentage of ECE-inhibition was expressed as $IC_{50}$ value (nM).

b) In vitro NEP-inhibitory activity.

The NEP-inhibitory activity in vitro was evaluated according to the method reported in the literature by C. Llorens. et al., Eur. J. Pharmacol., 69, (1981), 113–116.

Membranes from kidney cortex were prepared according to the following procedure.

By working at 0°-4° C. the kidneys were removed from killed male

Sprague-Dawley rats weighing approximately 300 g. Cortex was carefully dissected, finely minced and suspended in homogenization buffer (10 mM sodium phosphate pH 7.4 containing 1 mM $MgCl_2$, 30 mM NaCl, 0.02% NaNs) 1:15 weight/volume.

The tissue was then homogenized for 30 seconds using an Ultra-Turrax homogenizer.

Approximately 10 ml of homogenate were layered over 10 ml of sucrose (41% weight/volume) and centrifuged at 31200 rpm for 30 minutes at 4° C. in a fixed angle rotor.

The membranes were collected from the buffer/sucrose interface, washed twice with 50 mM TRIS/HCl buffer (pH 7.4) and resuspended into the same buffer for storage.

The membranes were stored in small aliquots at −80° C. until use. The NEP-inhibitory activity was evaluated by using the following method.

Aliquots of the membrane suspension prepared as above described (concentration 5 g/ml of proteins) were preincubated in the presence of an aminopeptidase inhibitor (Bestatin-1 mM) for 10 minutes at 30° C.

[$^3$H][Leus$^5$]-enkephaline (15 nM) and buffer TRIS/HCl pH 7.4 (50 mM) were added in order to obtain a final volume of 100 μl. Incubation (20 minutes at 30° C.) was stopped by adding 0.1M HCl (100 μl).

The formation of the metabolite [$^3$H]Tyr-Gly-Gly was quantified by chromatography on polystyrene columns (Porapak Q) and the percentage of inhibition of the metabolite formation was expressed as $IC_{50}$ value (nM).

The values of ECE-inhibitory activity and of NEP-inhibitory activity for some representative compounds of formula I are reported in the following table 1.

TABLE 1

ECE-inhibitory activity and NEP-inhibitory activity expressed as $IC_{50}$ values (nM) of the compounds 5, 6, 7, 9, 10, 11, 12, 13 in comparison to phosphoramidon and thiorphan, respectively.

| Compound | NEP $IC_{50}$ (nM) | ECE $IC_{50}$ (nM) |
|---|---|---|
| Thiorphan | 11.3 | — |
| Phosphoramidon | — | 50 |
| Compound 5 | 7.5 | 4 |
| Compound 6 | 10.3 | 4 |
| Compound 7 | 13.1 | 4 |
| Compound 9 | 22.5 | 2 |
| Compound 10 | 30.6 | 2 |
| Compound 11 | 37.4 | 13 |
| Compound 12 | 6.1 | 3 |
| Compound 13 | 10.7 | 2 |

The above reported results clearly show that the compounds of formula I, object of the present invention, are endowed with both ECE-inhibitory and NEP-inhibitory activity.

In particular, the NEP-inhibitory activity of the compounds of formula I is substantially comparable with that of thiorphan and the ECE-inhibitory activity is significantly greater than that of phosphoramidon.

What is claim is:

1. A compound of formula $$\text{HO}-\overset{\overset{O}{\|}}{\underset{\underset{Y}{|}}{P}}-X-CH-\overset{\overset{CH_2-R_1}{|}}{\underset{\underset{O}{\|}}{C}}-NH-Het-(CH_2)_n-R_2 \quad (I)$$

wherein

Y is a $C_1$-$C_4$ alkyl group or an OR group; R is a hydrogen atom, a $C_1$-$C_4$ alkyl group or a phenylalkyl group having from 1 to 4 carbon atoms in the alkyl moiety;

$R_1$ is a hydrogen atom, a phenyl group, a biphenyl group or a 5 or 6 membered heterocycle containing 1 or 2 heteroatoms selected from the group consisting of nitrogen, oxygen and sulphur, optionally substituted by one or two groups selected from the group consisting of $C_1$-$C_4$ alkyl or alkoxy groups, hydroxy, halogen and trifluoromethyl groups:

$R_2$ is a carboxylic group or a $COOR_3$ or $$\underset{\underset{R_5}{|}}{\overset{\overset{R_4}{|}}{CON}}$$

group; $R_3$ is a $C_1$-$C_4$ alkyl group or a phenylalkyl having from 1 to 4 carbon atoms in the alkyl moiety; $R_4$ and $R_5$, the same or different, are hydrogen atoms, $C_1$-$C_4$ alkyl or $C_5$-$C_7$ cycloalkyl groups;

n is 0 or 1;

Het is a heterocycle selected from the group consisting of thiazole, oxazole, isothiazole, isoxazole, pyrazole, imidazole, thiophene, pyrrole and pyridine;

X is NH or $CH_2$; or a pharmaceutically acceptable salt thereof.

2. A compound according to claim 1 wherein Y is a OR group, R is a hydrogen atom, a methyl or benzyl group and $R_2$ is a carboxylic group.

3. A compound according to claim 1 wherein Y is an OR group, R is a hydrogen atom, a methyl or benzyl group; $R_2$ is a carboxylic group; $R_1$ is phenyl and Het is a heterocycle selected between thiazole and pyridine.

4. A compound according to claim 1 wherein Y is a $C_1$–$C_4$ alkyl group; $R_2$ is a carboxylic group; $R_1$ is a phenyl group, optionally substituted by one or two halogen atoms, a biphenyl group or a heterocycle selected between thiazole and thiophene and Het is a heterocycle selected between thiazole, pyrrole and pyridine.

5. A compound according to claim 1 wherein Y is n.propyl; $R_2$ is a carboxylic group; $R_1$ is a phenyl group, optionally substituted by one or two halogen atoms, a 4-biphenyl group or a heterocycle selected between thiazole and thiophene and Het is a heterocycle selected between thiazole, pyrrole and pyridine.

6. A pharmacuetical composition containing a therapeutically effective amount of one or more compounds of formula I in admixture with a carrier for pharmaceutical use.

7. A method for the treatment of hypertension, renal failure and congestive heart failure comprising the administration of a therapeutically effective amount of a compound according to claim 1.

* * * * *